US011439499B2

(12) United States Patent
Wensrich et al.

(10) Patent No.: US 11,439,499 B2
(45) Date of Patent: Sep. 13, 2022

(54) INTRAOCULAR LENS INJECTOR

(71) Applicant: Alcon Inc., Fribourg (CH)

(72) Inventors: Douglas Brent Wensrich, Bedford, TX (US); Todd Taber, Fort Worth, TX (US); Len Takudzwa Magara, Pretoria (ZA); Jian Liu, Keller, TX (US)

(73) Assignee: Alcon Inc., Fribourg (CH)

( * ) Notice: Subject to any disclaimer, the term of this patent is extended or adjusted under 35 U.S.C. 154(b) by 321 days.

(21) Appl. No.: 16/507,393

(22) Filed: Jul. 10, 2019

(65) Prior Publication Data
US 2020/0015959 A1 Jan. 16, 2020

Related U.S. Application Data

(60) Provisional application No. 62/696,078, filed on Jul. 10, 2018.

(51) Int. Cl.
*A61F 2/16* (2006.01)

(52) U.S. Cl.
CPC ............ *A61F 2/167* (2013.01); *A61F 2/1678* (2013.01); *A61F 2002/1683* (2013.01)

(58) Field of Classification Search
CPC ...... A61F 2/167; A61F 2/1678; A61F 2/1667; A61F 2002/1683; A61M 5/31581
See application file for complete search history.

(56) References Cited

U.S. PATENT DOCUMENTS

| 5,494,484 | A | * | 2/1996 | Feingold | ............... A61F 2/167 206/5.1 |
| 5,873,879 | A | | 2/1999 | Figueroa et al. | |
| 7,156,854 | B2 | | 1/2007 | Brown et al. | |
| 2004/0059343 | A1 | * | 3/2004 | Shearer | ............... A61F 2/1664 606/107 |
| 2006/0229633 | A1 | * | 10/2006 | Shepherd | ............. A61F 2/1667 606/107 |
| 2009/0112223 | A1 | | 4/2009 | Downer | |
| 2013/0006259 | A1 | * | 1/2013 | Sanger | ............... A61F 2/1672 606/107 |
| 2014/0031832 | A1 | | 1/2014 | Catlin | |
| 2014/0257315 | A1 | | 9/2014 | Wu | |
| 2015/0066043 | A1 | | 3/2015 | Nallakrishnan | |
| 2015/0327992 | A1 | * | 11/2015 | Wagner | ............... A61F 2/1678 606/107 |
| 2016/0256316 | A1 | | 9/2016 | Van Noy et al. | |
| 2019/0224002 | A1 | * | 7/2019 | Springer | ............... A61F 2/1678 |

FOREIGN PATENT DOCUMENTS

| JP | 6278701 B2 | 2/2018 |
| WO | 9713476 A1 | 4/1997 |

* cited by examiner

*Primary Examiner* — Richard G Louis
*Assistant Examiner* — Chima U Igboko

(57) ABSTRACT

An intraocular lens (IOL) injectors and associated methods are described. The IOL injectors may include a collapsible portion configured to reduce the length of the IOL injector when the collapsible portion is altered from an uncollapsed configuration to a collapsed configuration. In some instances, an IOL may be advanced from a storage location to a dwell location when the collapsible portion is altered from the uncollapsed configuration to the collapsed configuration. The IOL injectors may also include a combination push and screw drive.

9 Claims, 15 Drawing Sheets

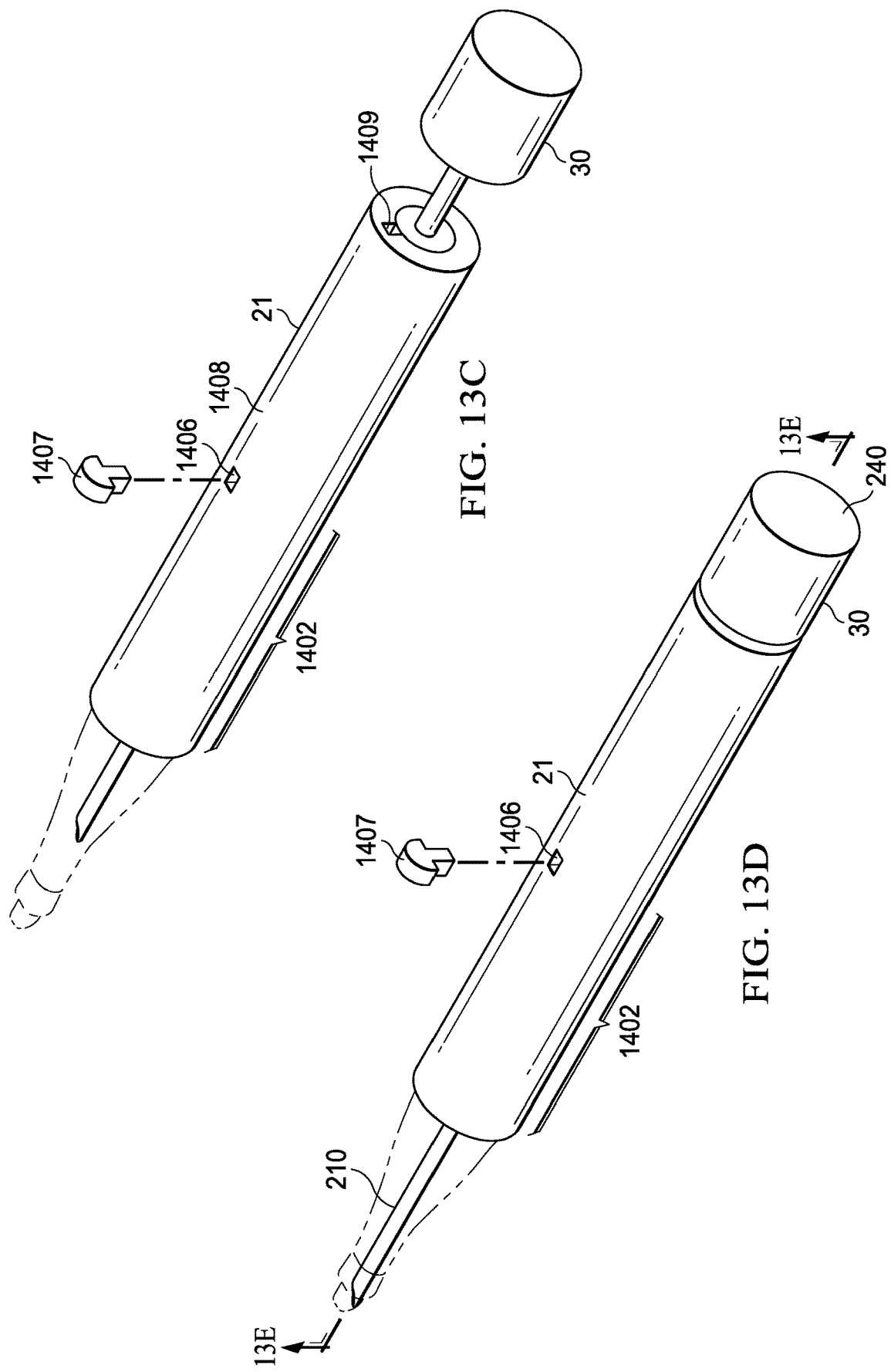

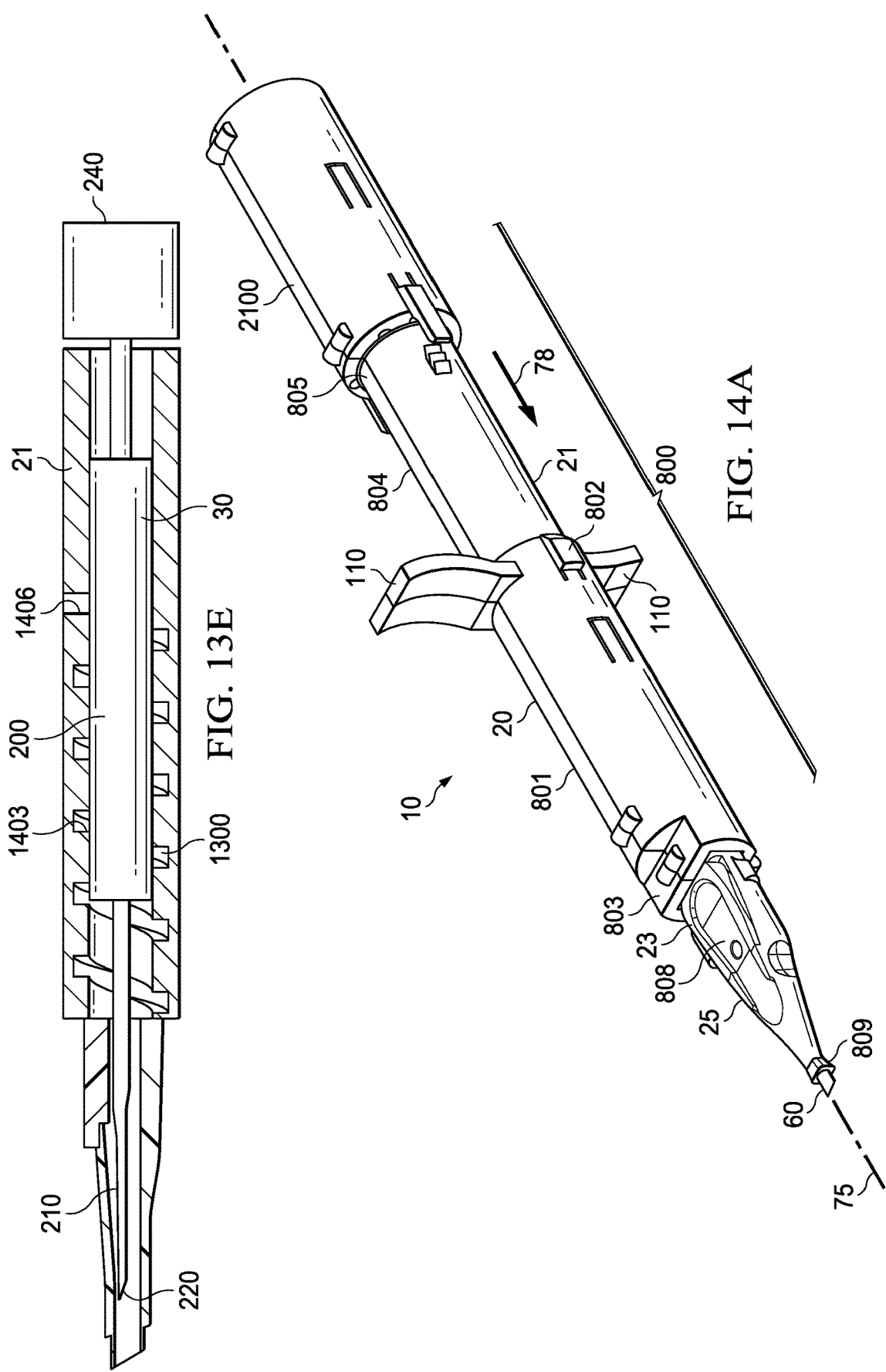

INTRAOCULAR LENS INJECTOR

CROSS-REFERENCE TO RELATED APPLICATIONS

This application claims the benefit of U.S. Provisional Application No. 62/696,078, filed Jul. 10, 2018, the entire contents of which are incorporated herein by reference.

TECHNICAL FIELD

The present disclosure relates to ophthalmic surgery, and more specifically, to intraocular lens (IOL) injectors and related methods.

BACKGROUND

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Light enters the human eye through a clear cornea that is located on the outer part of the eye and covers the pupil and iris. The light travels through the pupil and then encounters the lens, located behind the iris. As the light travels through the lens, the lens refracts the light so that it focuses on the retina, located in the back of the eye. Special cells in the retina detect the light and transmit signals based on the light via the optic nerve to the brain, which interprets the signals as vision.

Vision quality is, therefore, influenced by a number of factors, including the transparency and refractive properties of the cornea and the lens. Unfortunately, as people age or due to trauma or disease, the lens may be become less transparent and a cataract develops. Cataracts cause deterioration of vision and are often surgically corrected. During some cataract surgeries, the lens is surgically removed and replaced with an artificial intraocular lens (IOL).

Many cataractous lenses are removed by a surgical technique called phacoemulsification. During this procedure, an opening is made in the anterior capsule and a phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens, also referred to as an intraocular lens (IOL).

The IOL is injected into the eye through a small incision, sometimes the same incision used to remove the diseased lens. An IOL injector is used to deliver an IOL into the eye.

SUMMARY

According to a first aspect, the present disclosure relates to an intraocular lens (IOL) injector including an injector body and a plunger received into the injector body. The injector body may include a main body, a nozzle coupled to a distal end of the main body. The main body may include a bore and an interior wall defined by the bore. The interior wall may include a distal portion and a proximal portion. The nozzle may include a passage in fluid communication with the bore and a distal opening in fluid communication with the passage. The plunger may include a plunger body, a plunger rod coupled to a distal end of the plunger body, and a plunger tip formed at a distal end of the plunger rod and adapted to contact an IOL. One of the interior wall and the plunger body may include a threaded surface and the other of the interior wall and the plunger body may include a feature adapted to engage the threaded surface to produce axial movement of the plunger in response to axial movement or rotation of the plunger body. The interior wall may include a distal portion and a proximal portion, and the threaded surface or the feature adapted to engage the threaded surface may be disposed in the distal portion of the interior wall. The feature adapted to engage the threaded surface is a pin. The feature adapted to engage the threaded surface may be a second threaded surface. An aperture may be formed through the interior wall, and a pin may be adapted to be removably received within the aperture. The pin, when disposed in the aperture, may be adapted to prevent the threaded surface and the feature adapted to engage the threaded surface from engaging each other to produce axial movement of the plunger in response to axial movement or rotation of the plunger body. The threaded surface may include a pitch that varies along the main body. The pitch may be wider at a proximal end of the main body and may be narrower at a distal end of the main body. The plunger may also include a flange rotationally decoupled from the plunger body.

The feature adapted to engage the threaded surface may be a pin; the interior wall may include a distal portion and a proximal portion; the threaded portion may be formed in the distal portion of the interior wall; the plunger may include the pin; and the proximal portion of the interior wall may include a track extending from a proximal end of the main body to a proximal end of the threaded portion. The pin may be receivable into the track and moveable therealong. The interior wall may include a distal portion and a proximal portion. The plunger may be slideable through the bore along the proximal portion of the interior wall from a first location where the plunger tip is proximally adjacent to a storage location in the nozzle to a second position where the plunger tip is proximally adjacent to a dwell location. The second position may correspond to initial engagement of the threaded surface and the feature adapted to engage the threaded surface.

A collapsible portion may be disposed between the main body and the nozzle, the collapsible portion moveable between a collapsed configuration and an uncollapsed configuration. The collapsible portion may include a first sleeve and a second sleeve telescopingly received into the first sleeve. The collapsible portion may be moveable from the uncollapsed configuration in which the first sleeve is at a first position relative to the second sleeve to the collapsed configuration in which the first sleeve is at a second position relative to the second sleeve. The plunger tip may be moveable from a first plunger tip location to a second plunger tip location distal of the first plunger tip location when the collapsible portion is moved from the uncollapsed configuration to the collapsed configuration. The plunger may remain stationary relative to the main body when the collapsible portion is moved from the uncollapsed configuration to the collapsed configuration. A plunger cap may be removably coupled to the plunger and adapted to prevent engagement of the threaded surface and the feature adapted to engage the threaded surface. The injector body may include one or more tabs adapted to be engaged by one or more fingers. The tabs may be located closer to a distal end of the injector body than to a proximal end of the injector body.

BRIEF DESCRIPTION OF THE DRAWINGS

For a more complete understanding of the present disclosure and the associated features and advantages, reference is now made to the following description, taken in conjunction with the accompanying drawings, which are not to scale, and in which:

FIG. 13C shows the IOL injector of FIG. 13A in which the plunger is inserted into the bore formed in the injector body and a stop pin is removed from an aperture formed in the injector body;

FIG. 13D shows the IOL injector of FIG. 13A in a condition in which the plunger has been fully advanced within the bore formed in the injector body;

FIG. 13E is a partial cross-sectional view of the IOL injector of FIG. 13A taken along line 13E-13E in FIG. 13D and showing the plunger fully advanced in the bore formed in the injector body.

FIG. 14A is a perspective view of an exemplary IOL injector having a combination push and screw drive and a collapsible portion;

DETAILED DESCRIPTION

Figure 1:
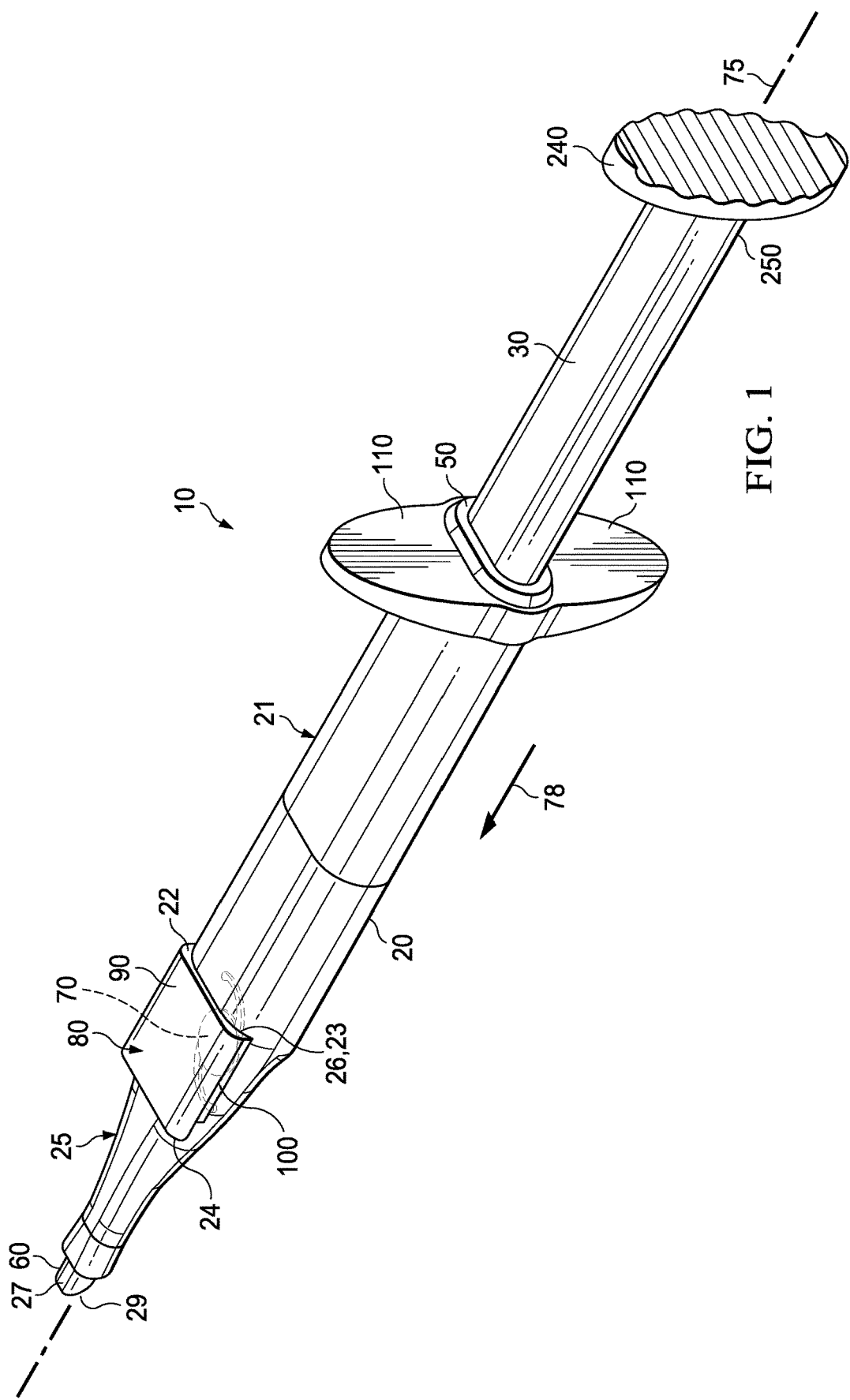
FIG. 1 is a perspective view of an example IOL injector.

In the following description, details are set forth by way of example to facilitate discussion of the disclosed subject matter. It should be apparent to a person of ordinary skill in the art, however, that the disclosed implementations are exemplary and not exhaustive of all possible implementations.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to ophthalmic surgery, and more specifically, to an intraocular lens (IOL) injector.

Following removal of a cataractous lens by phacoemulsification, the cataractous lens is replaced by an artificial lens, referred to herein as an IOL. The IOL is typically injected into the eye through the same small incision used to remove the diseased lens. An IOL injector is used to deliver an IOL into the eye.

Figure 2:
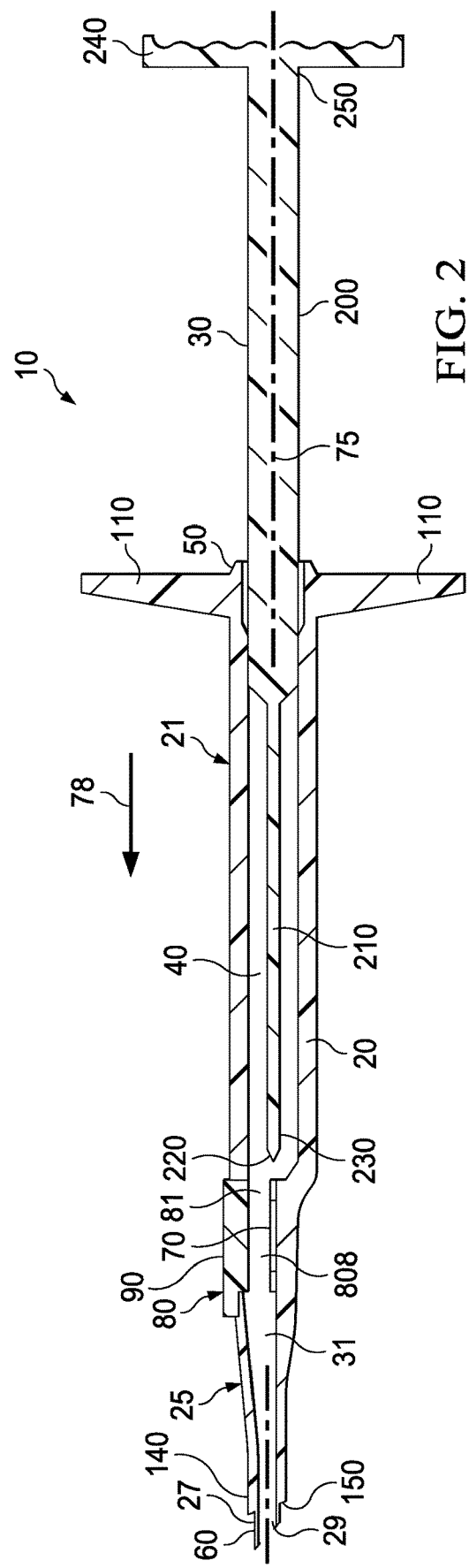
FIG. 2 is a longitudinal cross-sectional view of the exemplary IOL injector of FIG. 1.

FIGS. 1 and 2 are schematics of an exemplary IOL injector 10. The IOL injector 10 has an injector body 20. The injector body 20 includes a main body 21 having a proximal end 50 and a distal end 22. The injector body 20 includes a nozzle 25 having a proximal end 23 and a distal end 60. The nozzle 25 defines a passage 31. The proximal end 23 of the injector nozzle 25 is coupled to the distal end 22 of the main body 21. A distal portion of the injector body 20 includes an IOL storage compartment 80 that defines a cavity 81 operable to house an IOL 70 prior to insertion into an eye. The nozzle 25 also includes a distal tip 27 that defines an opening 29 through which the IOL is delivered out of the IOL injector 10. In some implementations described herein, the storage compartment 80 defines an IOL storage location 80S. The IOL storage compartment 80 has a proximal end 26 and a distal end 24, the proximal end 26 of the IOL storage compartment 80 being coupled to the distal end 22 of the main body 21. In some instances, a door 90 may be included to provide access to the IOL storage compartment 80. The door 90 may include a hinge 100 such that the door 90 may be pivoted about the hinge 100 to open the IOL storage compartment 80. The injector body 20 defines a bore 40 that joins and is fluid communication with the opening 29. A longitudinal axis 75 extends along the bore 40. The bore 40 extends through the main body 21 and the nozzle 25. The portion of the bore in the main body 21 may be referred to as the main body bore, and the portion of the bore in the nozzle 25 may be referred to as the nozzle bore. The injector body 20 may also include tabs 110, for example formed at the proximal end 50 of the main body 21. Other configurations are possible. For example, in other implementations, the tabs 110 may be located at the distal end 22 of the main body 21. The tabs 110 may be manipulated by fingers of a user, such as an ophthalmologist or other medical professional, to advance the plunger 30 (discussed below) through the bore 40.

In some implementations, for example as shown in FIG. 14A, a length of one of the tabs 110 extends from the injector body 20 (e.g., perpendicularly from the longitudinal axis 75) a shorter distance than another of the tabs 110, such that a user is able to comfortably hold the IOL injector body 20 in one hand while rotating the plunger body 200 with the other hand. In some implementations, at least one of the tabs 110 may have a length less than 2.0 cm.

In some implementations, various manipulations of the IOL injector 10, and various method steps, may be performed by one person, or by a plurality of persons. For example, some steps of methods described herein may be performed by a nurse, while other steps may be performed by an ophthalmic surgeon. For example, advancing an IOL 70 within the injector body 20 of an IOL injector 10 from a storage location 808 to a dwell location 809 (as shown, for example, in FIG. 9) may be performed by a nurse, while injection of the IOL 70 into an eye may be performed by a surgeon.

The IOL injector 10 also includes a plunger 30 received within the bore 40 and moveable therein such that the plunger 30 is slideable within the bore 40. As the plunger 30 is displaced distally within bore 40, the plunger 30 engages and advances an IOL, such as IOL 70, contained in the compartment 80.

As shown in FIG. 2, the plunger 30 includes a plunger body 200, a plunger rod 210 extending distally from the plunger body 200, and a plunger tip 220 formed at a distal end 230 of the plunger rod 210 and adapted to contact an IOL disposed, for example, within the IOL storage compartment 80 of the IOL injector 10. The plunger 30 may also include a flange 240 formed at a proximal end 250 of the plunger body 200. The plunger 30 is movable along the bore 40 in response to an axial force applied to the plunger 30 in the direction of arrow 78. The axial force may be applied to the flange 240, such as by a thumb of a user.

In some implementations described herein, various parts of the plunger 30 may be physically separated or decoupled from each other within the injector body 20 of the IOL injector 10. For example, in some implementations, the plunger body 200 may be physically separated or decoupled from the plunger rod 210. In various implementations, where various parts of the plunger 30 are physically separated or decoupled from each other, additional components of the IOL injector 10 may actuate movement of one part of the plunger 30 in response to movement of another part of the plunger 30.

Figure 3:
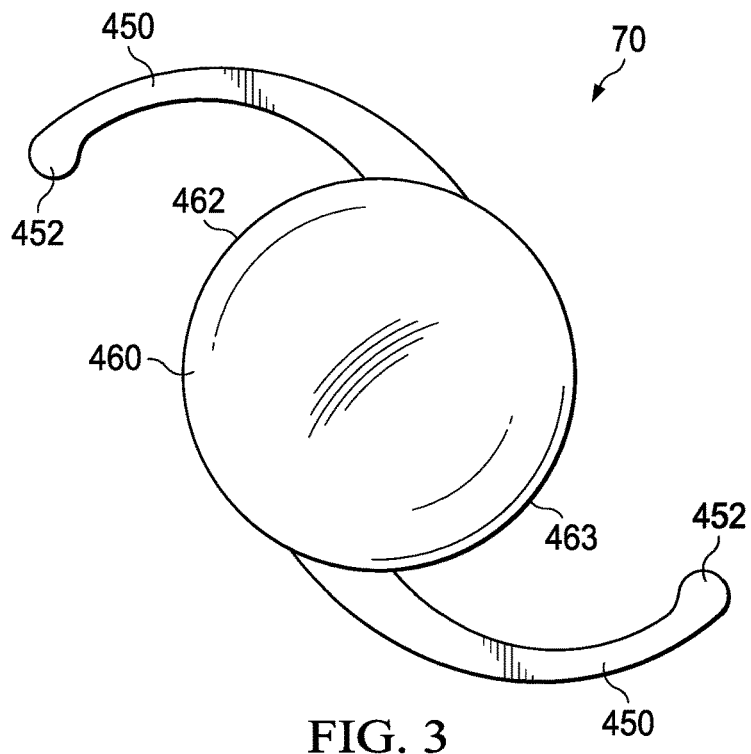
FIG. 3 shows an exemplary one-piece IOL.

In some implementations, the IOL 70 may be a one-piece IOL. That is, in some implementations, the IOL 70 may include an optic 460 and haptics 450, as shown in FIG. 3. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye. The optic 460 includes a distal edge 462 and a proximal edge 463

Figure 4:
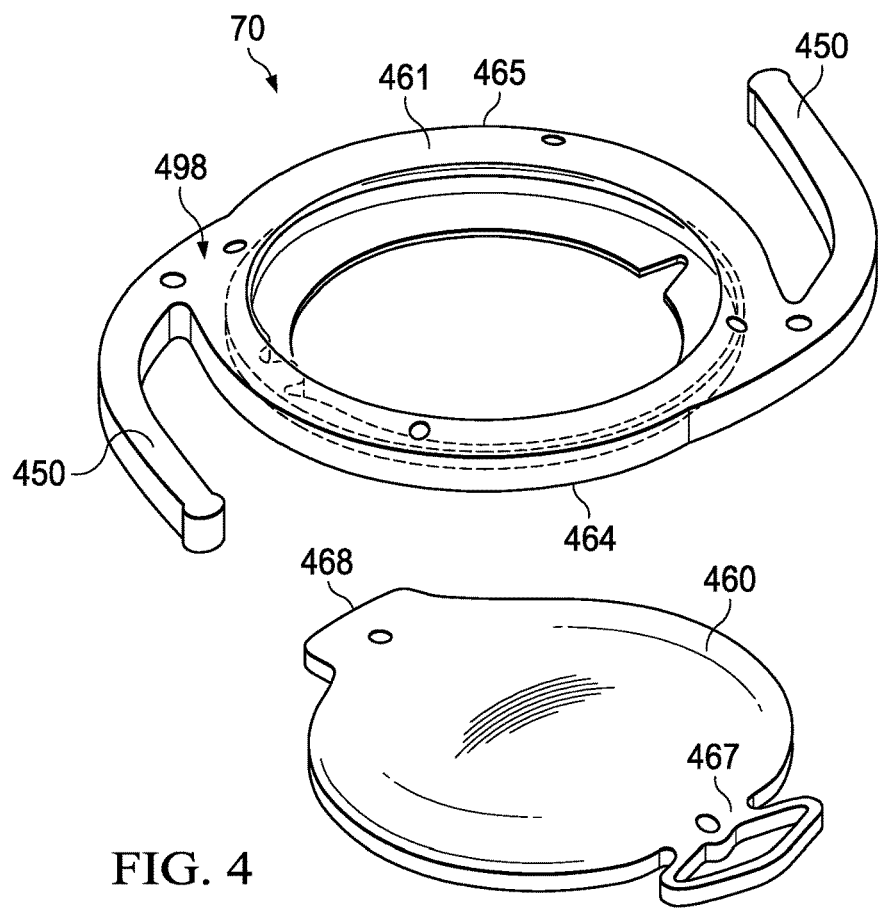
FIG. 4 shows an exemplary two-piece IOL including a base and an optic.

In other implementations, the IOL 70 may be a multi-piece IOL. For example, in some implementations, the IOL 70 be include two or more separate components. FIG. 4 is an example IOL 70 that includes two removably attached components. As shown in FIG. 4, the IOL 70 includes an optic 460 and a base 461 that includes haptics 450. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 4, are separately injectable into a patient's eye. Once in the eye, the components may be assembled into a complete IOL. For example, the two-piece IOL 70 shown in FIG. 4, the optic 460 and the base 461 are separately injectable into an eye. Once injected, the optic 460 is adapted to be coupled to and to rest on the base 461. The base 461 includes a distal edge 464 and a proximal edge 465. The optic 460 includes a distal edge 467 and a proximal edge 468.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single-piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into the IOL storage compartment of the IOL injector, such as the IOL storage compartment 80 of the IOL injector described above. As also explained, the storage compartment may be accessed via a door, such as the door 90. In some implementations, the IOL may be manually folded into a compressed or folded configuration prior to installation into the IOL injector.

In the case of a two-piece IOL, in some implementations, a user may load the base (which may be similar to base 461) into an IOL storage compartment of an IOL injector, for example, via a door. The optic (which may be similar to optic 460) of may be introduced into the IOL storage compartment of separate IOL injector, for example, via a door. In some instances, the IOL storage compartment may be accessed through the door similar to door 90. In some implementations, one or both of the base and the optic may be manually folded into a compressed or folded configuration prior to installation into the IOL injector.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed and already contained within the IOL injector when the IOL injector is received by the user. For example, the IOL may be installed during manufacturing and prior the IOL injector being shipped to an end-user. The IOL injector(s) may be packaged within sterile packaging when received by a user.

As would be understood by persons of ordinary skill in the art, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. Manual installation and folding of an IOL may also introduce the possibility of contamination of the IOL, such as by human error or poor sterile technique. Contamination of the IOL may compromise the sterile environment for the patient and risk infection or other harm to the patient.

Figure 5:
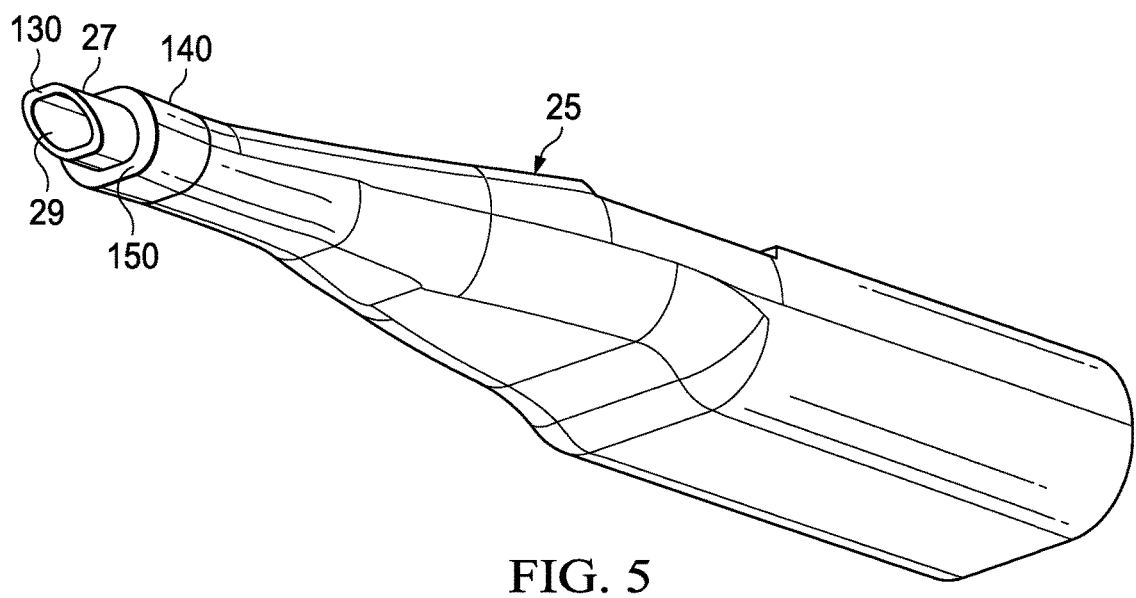
FIG. 5 is a perspective view of an exemplary nozzle of an IOL injector.
Figure 6:
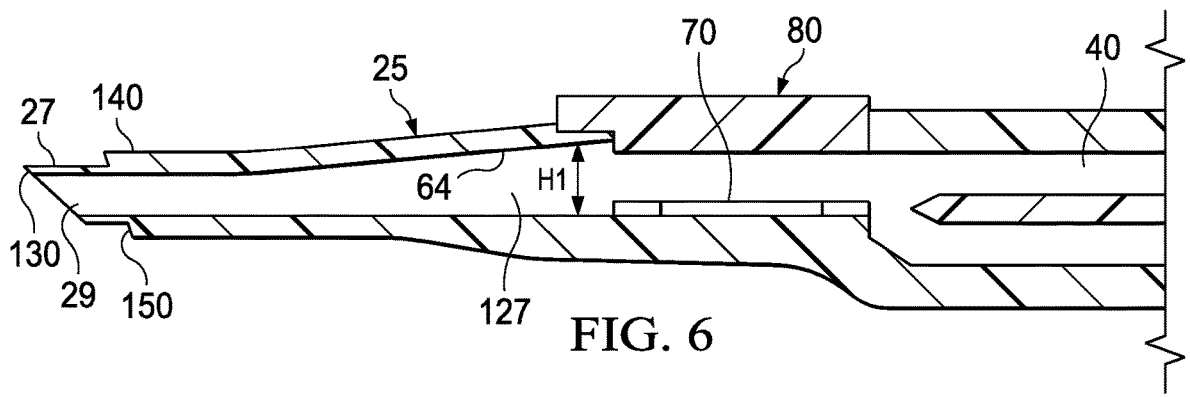
FIG. 6 is a cross-sectional view of the exemplary nozzle of an IOL injector shown in FIG. 5.
Figure 7:
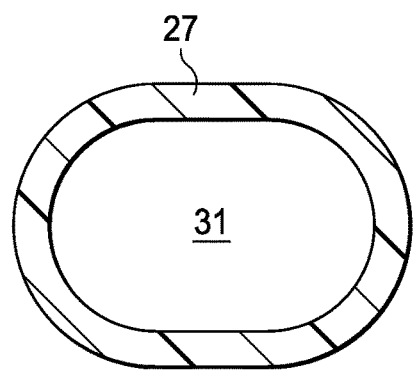
FIG. 7 is an exemplary cross-sectional view of a distal tip of a nozzle of an IOL injector.

FIGS. 5-7 illustrate details of the exemplary nozzle 25. In some instances, the nozzle 25 has a tapered exterior surface. Further, the passage 31 of the nozzle 25 may form part of the bore 40. The passage 31 tapers towards the opening 29. The distal tip 27 is adapted for insertion into an eye so that an IOL may be implanted. An IOL is expelled from the opening 29 formed in the distal tip 27. As shown in FIG. 7, the distal tip 27 may have an elliptical cross section. Additionally, the distal tip 27 may include a beveled tip 130. The cavity 81 of the storage compartment 80, passage 31, and opening 29 may define a delivery passage 127. A size of the delivery passage 127 may vary along a length thereof. That is, in some instances, a height H1 of the delivery passage 127 may change along a length thereof. The variation in size of the delivery passage 127 may contribute to the folding of the IOL as it is advanced therealong.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 8:
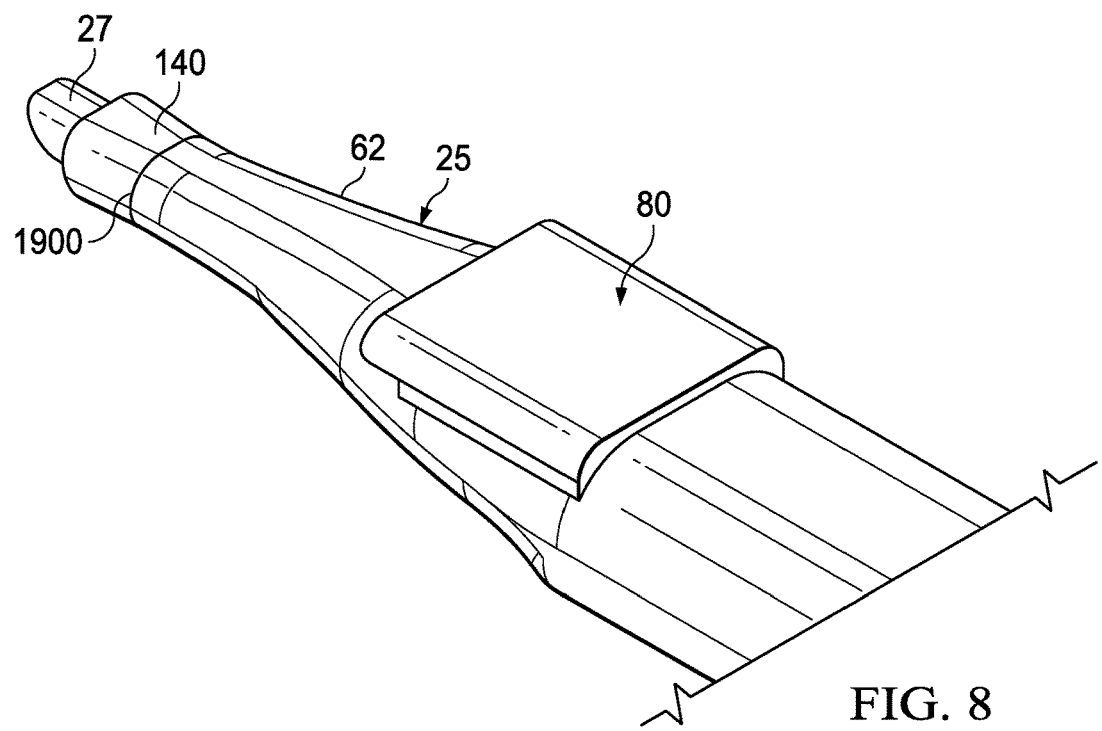
FIG. 8 is a detail view of an exemplary nozzle.

FIG. 8 is a detail view of a portion of the exemplary nozzle 25. The nozzle 25 may include a tapered portion 62 and the insertion depth guard 140. The distal tip 27 may include a demarcation 1900 that provides a visual indication of the dwell location 809 (shown, for example, in FIG. 9) of the folded or partially folded IOL 70. The term "dwell location" as used herein refers to a location adjacent to the distal end 60 of the nozzle 25 where an IOL would reside prior to being ejected from the IOL injector. For example, in some implementations, the dwell location 809 may be a location between 2 mm and 10 mm from the distal end 60. An IOL may be placed in dwell location prior to a surgical procedure. The IOL may be placed in the dwell location such as by a nurse or other medical professional that prepares the IOL injector for use. Placing an IOL in a dwell location provides for folding an IOL, either partially or fully, and for a decreased travel distance of the IOL when a physician takes possession of the IOL for implantation of the IOL into a patient's eye. Thus, placing an IOL placed at the dwell location may be a preparatory step performed by an assistant to a surgical procedure that allows the physician more quickly to perform the surgical procedure once the physician takes possession of the IOL injector. For example, in the example shown in FIG. 8, the demarcation 1900 is a narrow ridge or line that encircles all or a portion of the nozzle 25. In some instances, the demarcation 1900 may be formed into the nozzle 25, such by a recess or groove or a protruding ridge. In other implementations, the demarcation 1900 may be formed by a paint or other coating or an additive or insert applied to the material forming the nozzle 25, such as during manufacturing or sometime thereafter. In some instances, the demarcation 1900 may be disposed between the tapered portion 62 and the insertion depth guard 140. In implementations in which a depth guard 140 is omitted, the demarcation 1900 may located between the distal tip 27 and the tapered portion 62. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as the IOL is moved therethrough by the plunger 30.

Figure 9:
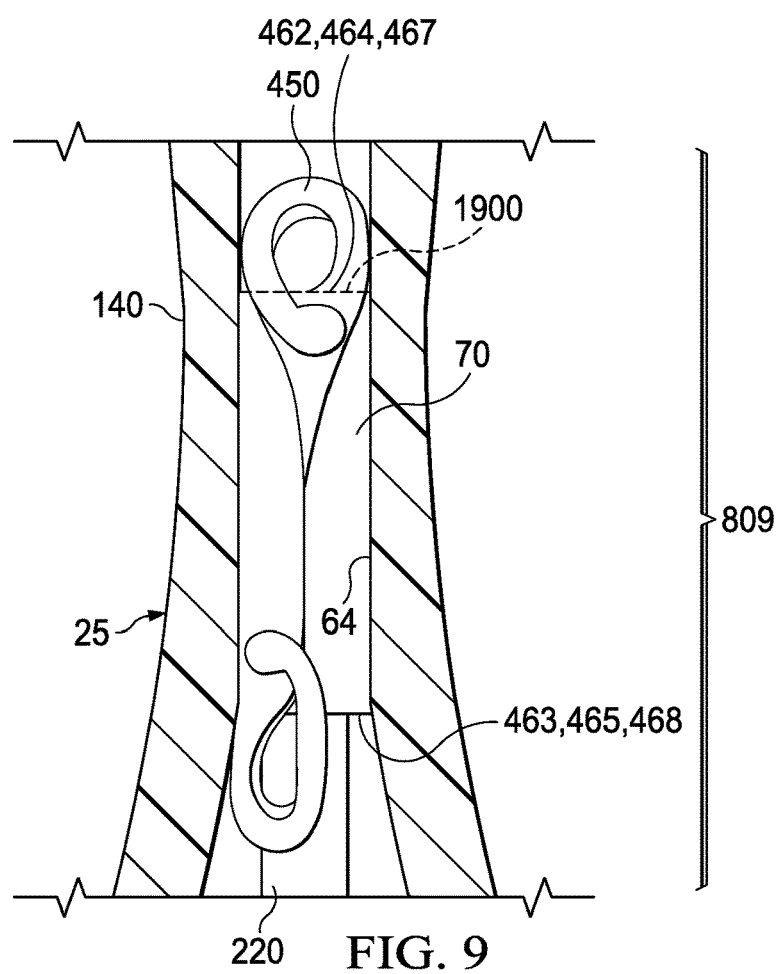
FIG. 9 is another detail view of a cross-section of an exemplary nozzle showing an IOL located at a dwell position.

FIG. 9 shows a view of the exemplary nozzle 25 with the IOL 70 located therein at the dwell location 809. A plunger 220 is shown contacting the proximal edge 463, 465, or 468. As shown in FIG. 9, the dwell location 809 of the IOL 70 may be defined as a location where a distal edge 462 of the optic 460 of the MI, 70 aligns with the demarcation 1900. In the case of a two-piece IOL, such as IOL 70 shown in FIG. 4, where the base 461 and optic 460 are implanted into an eye separately, the dwell location 809 of the two-piece IOL 70 may be defined as a location where a distal edge 467 of the optic 460 or the distal edge 464 of the base 461 aligns with the demarcation 1900. A haptic 450 or a portion thereof may extend beyond the demarcation 1900. Further, although FIG. 9 shows the IOL 70 as including haptics 450, it is understood that the IOL 70 shown in FIG. 9 may also represent the optic 460 of a two-piece IOL, such as the two-piece IOL 70 shown in FIG. 4, which omits haptics.

Due to the sensitivity and delicacy of ocular tissues and structures, it is important that the user be able to advance the IOL 70 through an IOL injector with an acceptable peak or maximum speed and force. In some existing IOL injectors, when folding and advancing the IOL into the eye, there is typically a high peak axial force that must be applied, e.g., by a user, just before the IOL is expelled from the IOL injector. However, as the IOL begins to emerge from the IOL injector, the force required to continue to advance the IOL rapidly reduces. As a result, in some cases, the larger change force needed to advance the IOL may cause the IOL 70 to be ejected with high velocity in a less controllable manner. For example, the user may be unable to react quickly enough to the change in resistance associated with advancement of the IOL. The changes in resistance to advancement experienced by the IOL just prior to expelling the IOL from the IOL injector and the difficulty experienced by a user in reacting quickly to these changes in resistance in order to avoid a rapid ejection of the IOL from the IOL injector may reduce user control of the IOL injector and ultimately the IOL delivery. The challenges of delivering an IOL include ensuring that the magnitude of force applied through user interaction be consistent, repeatable, and at a desirable level. It is also important to have an IOL injector that is intuitive and capable of being utilized by users having varying levels of skills and techniques.

The present disclosure describes an IOL injectors having a combination push and screw drive operable to advance an IOL through the IOL injectors. The IOL injectors of the present disclosure have a combination push and screw drive having a threaded portion adapted to advance an IOL in response to either an axial push on a flange of the plunger or rotation of a plunger body of the plunger.

Figure 10:
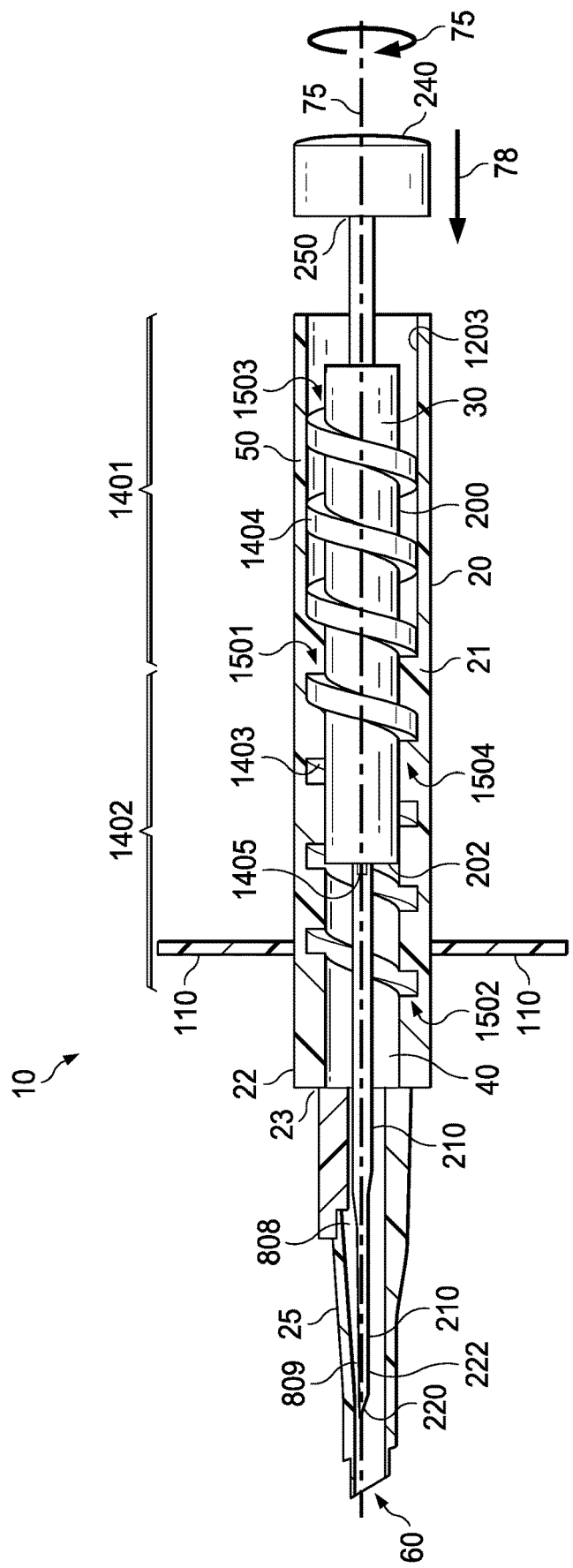
FIG. 10 is a cross-sectional view of an exemplary IOL injector having a combination push and screw drive and with a threaded surface of a plunger partially engaged with a threaded surface of an injector body.

FIG. 10 is a partial cross-sectional view of an exemplary IOL injector 10 having a combination push and screw drive. The IOL injector includes an injector body 20. The injector body 20 includes a main body 21 having a proximal end 50 and a distal end 22; a nozzle 25 having a proximal end 23 and a distal end 60, the proximal end 23 of the nozzle 25 being coupled to the distal end 22 of the main body 21; and a bore 40 extending through the injector body 20. A longitudinal axis 75 extends along the bore 40. Although not illustrated in FIG. 10, the IOL injector 10 may also include a storage compartment, similar to the storage compartment 80 described above, and may also include a door, which may be similar to door 90, in order to access the storage compartment, e.g., to install or remove an IOL from a cavity of the storage compartment.

The main body 21 includes an interior wall 1203 having a proximal non-threaded portion 1401 and a distal threaded portion 1402. The threaded portion 1402 includes a threaded surface, referred to hereinafter as bore thread 1403, that is adapted to engage with a threaded surface formed on a plunger, referred to hereinafter as plunger thread 1404 and described in more detail below. This threaded engagement provides axial displacement of the plunger in response to a rotation of the plunger.

The IOL injector 10 also includes a plunger 30 movably within the bore 40. In some instances, the bore 40 and, therefore, the plunger 30 may be concentrically disposed within the injector body 20. The plunger 30 includes a plunger body 200; a plunger rod 210 extending from a distal end 202 of the plunger body 200; a plunger tip 220 formed at a distal end 222 of the plunger rod 210 and adapted to contact an IOL; and a flange 240 disposed at a proximal end 250 of the injector body 200. A plunger thread 1404 is formed along at least a portion of the injector body 200. The plunger thread 1404 is adapted matingly to engage the bore thread 1403 formed on the interior wall 1203 of the main body 21 to cause the injector 30 to axially advance in response to a rotation of the plunger 30 relative to the main body 21. The plunger rod 210 is rotationally decoupled from the plunger body 200, e.g. by an axle 1405, such that rotation of the plunger body 200 does not cause rotation of the plunger rod 210. Other types of linkages that permit rotation of the plunger body 200 relative to the plunger body 210 may also be used.

The plunger body 200 is slidably movable within the non-threaded portion 1401 of the bore 40 in response to an axial force applied to the plunger 30, e.g., to the flange 240, in the direction of arrow 78 until the plunger thread 1404 of the injector body 200 engages with the bore thread 1403 of the main body 21. With the threaded surfaces engaged, the plunger body 200 is rotatably and axially movable within the threaded portion 1402 of the bore 40 in response to an axial force applied to the plunger 30, e.g., to the flange 240, in the direction of the arrow 78 or in response to a rotation of the plunger body 200, e.g., a rotation in the direction of arrow 75.

The nozzle 25 includes an IOL storage location 808 and an IOL dwell location 809 distal to the IOL storage location 808. The bore thread 1403 has a proximal end 1501 and a distal end 1502, and the plunger thread 1404 has a proximal end 1503 and a distal end 1504. In some implementations, the plunger tip 220 is movable from a first position proximally adjacent to the IOL storage location 808 to a second position proximally adjacent to the IOL dwell location 809 in response to an axial force applied to the plunger 30, e.g., to the flange 240, in the direction of arrow 78. The first position may correspond to a position of the plunger 30 when initially inserted into the bore 40. The second position may correspond to a position of the plunger 30 when the distal end 1504 of the plunger thread 1404 initially engages the proximal end 1501 of the bore thread 1403, e.g., when the plunger thread 1404 of the plunger body 200 begins to engage the bore thread 1403 of the main body 21. In some implementations, the plunger tip 220 is movable from the second position proximally adjacent to the IOL dwell location 809 to the distal end 60 of the nozzle 25 in response to an axial force applied to the plunger 30, e.g., to the flange 240, in the direction of the arrow 78 or in response to a rotation of the plunger body 200, e.g., a rotation in the direction of arrow 75.

In some implementations, when positioned at the first position, the plunger tip 220 may be positioned 5 to 20 mm proximal to an IOL disposed in the storage location 808, and, when positioned at the second position, the plunger tip 200 may be positioned immediately proximally adjacent to and in contact with a single-piece IOL or a ring or an optic of a multi-piece IOL (e.g., a two-piece IOL) with the single-piece or component of a multi-piece IOL is positioned relative to the dwell location 809 as described above with respect to FIG. 9. As described herein, for example, the dwell location 809 may be indicated by positioning of the IOL 70, or part thereof, relative to the demarcation 1900.

Figure 11A:
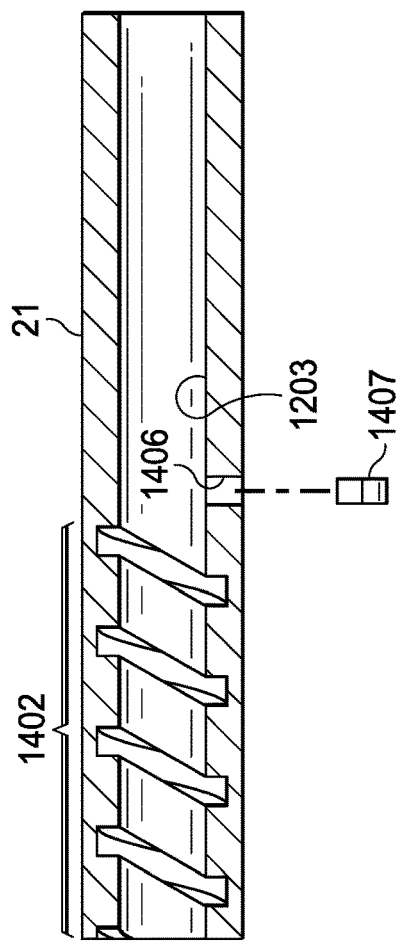
FIG. 11A is a cross-sectional view a main body of an exemplary IOL injector having a combination push and screw drive and a hard-stop.
Figure 11B:
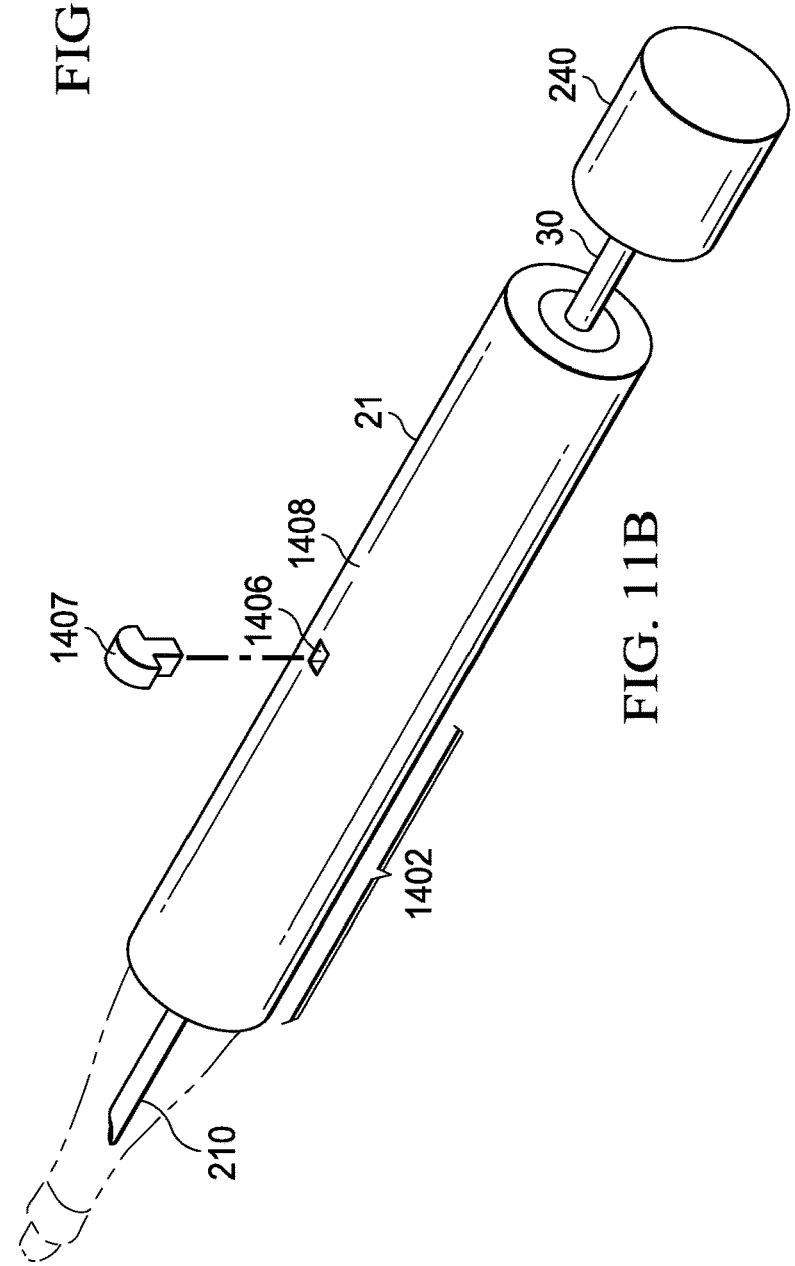
FIG. 11B is a perspective view of an example IOL injector with a nozzle omitted.

FIG. 11A shows a cross-sectional view of an example main body 21 of an IOL injector 10. FIG. 11B shows a perspective view of an IOL injector 10 that includes the main body 21 shown in FIG. 11A with the nozzle omitted. The main body 21 includes a removable pin 1407 that is received into an aperture 1406 formed in the main body 21 and that extends between interior wall 1203 and exterior surface 1408 of the main body 21. When installed into the main body 21, the pin 1407 is operable to engage a portion of the plunger 30, e.g., the distal end 1504 of the plunger thread 1404, and functions as a hard stop to prevent additional axial movement of the plunger 30 when the plunger 30 reaches the second position. With the removable pin 1407 installed in the aperture 1406, the removable pin 1407 prevents engagement, or inadvertent engagement, of the plunger thread 1404 with the bore thread 1403. With the removable pin 1407 removed from the aperture 1406, the plunger thread 1404 is able to engage the bore thread 1403. In some implementations, placement of an IOL in the dwell location 809 may correspond to engagement of the distal end 1504 of the plunger thread 1404 with the removable pin 1407

Figure 12:
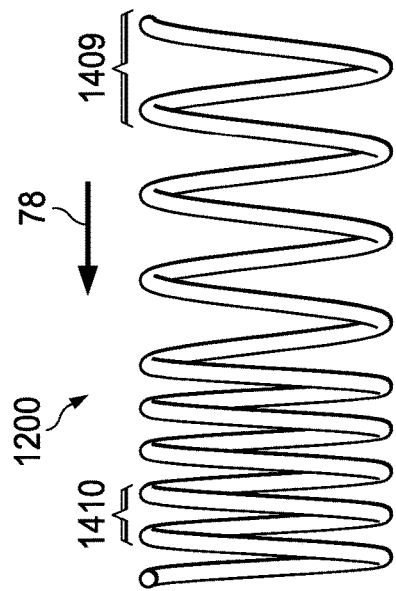
FIG. 12 shows an exemplary variable pitch thread.

In some implementations, the bore thread 1403 may have a pitch that varies along a length of the bore 40. In some implementations, the plunger thread 1404 may have a pitch that varies along a length of the main body 21 of the plunger 30. The pitch of a thread is the distance, measured parallel to the axis of the thread, between corresponding points on adjacent surfaces, in the same axial plane. Thus, the pitch may be considered to be the distance between adjacent crests of the thread. FIG. 12 shows a schematic of an exemplary variable pitch thread 1200, which may refer herein to thread of the bore thread or the plunger thread. For example, a relatively narrow pitch is indicated by 1409 and a relatively wide pitch is indicated by 1410. In order to take advantage of a variable pitch threaded surface formed on an inner surface of an IOL injector, the plunger would need a thread follower as opposed to a threaded surface, as shown with respect to FIGS. 13A and 13B, for example, and discussed in more detail below. A thread follower may be in the form of a pin or protrusion extending from a surface of the plunger.

In some implementations, a bore thread may have a pitch that is wider at a proximal end of the thread than at a distal end of the thread. As a result of a variable pitch thread, an axial speed of a plunger through the injector body would vary for a given rotational speed. Accordingly, if the direction of arrow 78 in FIG. 12 indicated a distal direction, axial movement of a plunger engaged with the thread 1200, for a given rotational speed, would have a faster axial speed where the plunger initially engages the thread 1200 but would slow during final advancement of an IOL out of the injector and into the eye. Having a variable pitch thread in which the pitch is narrower at the distal end that slows axial movement for a given rotational speed, a greater number of revolutions of the plunger about the rotational axis is required to advance the plunger axially toward the distal end of the nozzle. For example, the variable pitch thread may have a pitch from, or from about, 5 mm to 10 mm at the distal end, and may have a pitch from, or from about, 15 mm to 30 mm at the proximal end.

In some implementations, the bore 40 may lack a non-threaded portion 1401. In these implementations, the bore thread 1403 may extend to the proximal end 50 of the main body, and the plunger body 200 of the plunger 30 may also have a plunger thread 1404 that extends to the distal end 202 of the plunger body 200. Accordingly, in some implementations, the IOL plunger thread 1404 and the bore thread 1403 engage immediately upon insertion of the plunger 30 into the main body 21 of the injector 10. In such implementations, the plunger body 200 is rotatably and axially movable within the threaded portion 1402 of the bore 40 in response to an axial force applied to the plunger 30, e.g., applied to the flange 240, in the direction of the arrow 78 or in response to a rotation of the plunger body 200, e.g., rotation in the direction of arrow 75. In these implementations, the plunger tip 220 is movable from the second position proximally adjacent to the IOL dwell location 809 to the distal end 60 of the nozzle 25 in response to an axial force applied to the flange 240 in the direction of the arrow 78 or in response to a rotation of the plunger body 200, e.g., rotation in the direction of arrow 75. Further, in some implementations, the bore thread 1403 may have a variable pitch in which the pitch of the bore thread 1403 is wider at the proximal end 1501 than at the distal end 1502. In such implementations, for a given rotational speed of the plunger body 200, axial movement of the plunger 30 is faster to advance the IOL 70 from the storage location 808 to the IOL dwell location 809 and is slower during the final advancement of the IOL 70 from the IOL dwell location 809 into the eye.

In some implementations, the flange 240 may be retained onto the plunger body 200 but rotationally decoupled therefrom. Accordingly, rotationally decoupling the flange 240 from the plunger body 200 allows axial force to be applied to the flange 240 without the flange 240 itself rotating when the plunger thread 1404 is engaged with the bore thread 1403. For example, in some implementations, the flange 240 may be a disc rotatably coupled to the distal end 250 of the plunger body 200 of the plunger 30, e.g., via an axle coupling.

Figure 13A:
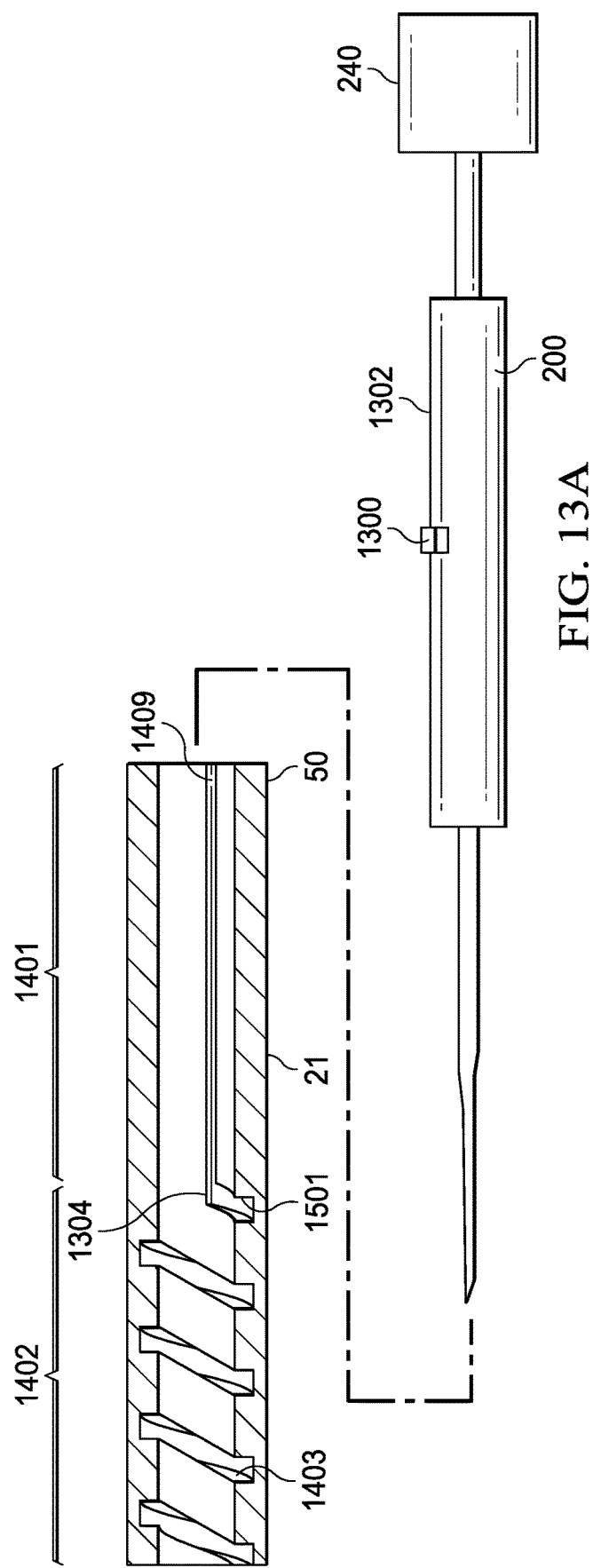
FIG. 13A shows an exemplary IOL injector having a combination push and screw drive in which the plunger is removed from the injector body.
Figure 13B:
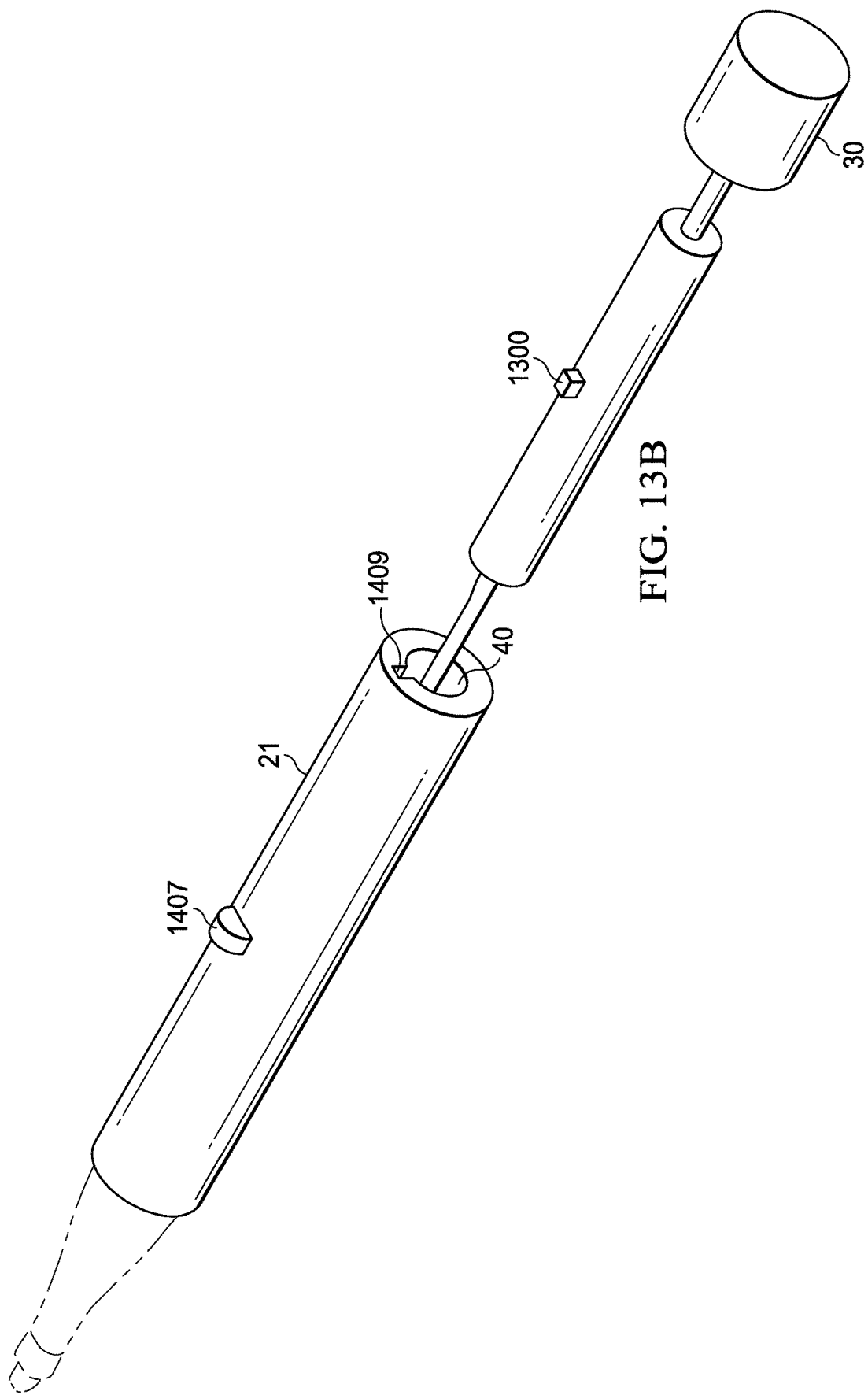
FIG. 13B shows the IOL injector of FIG. 13A in which the plunger is being inserted into a bore formed in an injector body and in which a stop pin is received into the injector body.

Referring to FIGS. 13A-13C, in some implementations, as explained above, the plunger thread 1404 may be replaced with a pin 1300 formed or otherwise disposed on exterior surface 1302 of the plunger body 200. A cross-sectional shape of the pin 1300 may correspond to a cross-sectional shape of the bore thread 1403. The pin 1300 is adapted to engage with and move within the bore thread 1403.

The pin 1300 is sized to fit within the dimensions of the bore thread 1403. For example, in some implementations, the pin 1300 may have a length and/or a width of about 1 mm to 2 mm. In some implementations, the bore thread 1403 may have a variable pitch. The pin 1300 may be sized to move with the variable pitch bore thread 1403.

Additionally, in some implementations, the non-threaded portion 1401 of the main body 21 may have a linear track 1409 extending from the proximal end 50 of the main body 21 to the proximal end of the threaded portion 1402, which may correspond to the proximal end 1501 of the bore thread 1403. The track 1409 may be aligned with the longitudinal axis 75 of the bore 40. The track 1409 is adapted to receive the pin 1300 and allow linear movement of the pin 1300 and, by extension, the plunger body 200, in the non-threaded portion 1401. The track 1409 joins with the bore thread 1403 at a junction 1304, allowing the plunger body 200 to follow the bore thread 1403.

FIGS. 13B and 13C show an example IOL injector 10, in which a nozzle is omitted, that includes a combination push and screw drive. The IOL injector 10 includes both a plunger thread 1404 and adjoining a track 1409 formed in a main body 21, a pin 1300 disposed on the plunger body 200 and adapted to follow the track 1409 and the bore thread 1403, and a removable pin 1407 adapted to be removably received into an aperture 1406 formed in the main body 21. The track 1409 may be linear. The aperture 1406 is located at the proximal end of the threaded portion 1402, which corresponds to the proximal end 1501 of the bore thread 1403. The pin 1407 defines a hard stop that, when inserted into the aperture 1406, prevents advancement of the plunger body 200 along the threaded portion 1402 of the main body 21.

FIG. 13C shows the plunger 30 inserted into the main body 21 and the pin 1407 removed from the aperture 1406. FIG. 13D shows the plunger 30 fully advanced in the main body 21. FIG. 13 is a cross-sectional view taken along line 13E-13E in FIG. 13D.

Although FIGS. 13A-13D illustrate and example in which threads are formed on an inner surface of the main body of an injector body and a pin formed on the plunger body, the scope of the disclosure is not so limited. In other implementations, a pin operable to engage a threaded surface may be formed on an inner surface of an injector body and a threaded surface adapted to engage the pin may be formed on an exterior surface of the plunger. The pin and the threaded surface cooperate to advance the plunger axially when an axial force is applied to the plunger or when the plunder is rotated.

Figure 15:
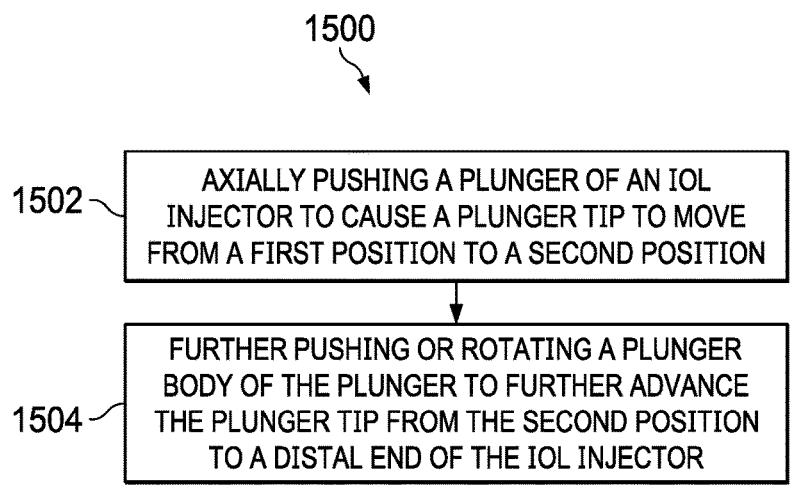
FIG. 15 is an example method of using an IOL injector.

The present disclosure also relates to methods of dispensing an IOL from an IOL injector. The IOL may be dispensed from the IOL injector into an eye. An example method is shown in FIG. 15. At 1502, the method includes axially pushing a plunger, causing the plunger tip to move from the first position to the second position. At 1504, the method includes further axially pushing the plunger or rotating the plunger body of the plunger 30 to further advance the plunger tip from the second position to a distal end of the IOL injector, such as a distal end of a nozzle 25 of the IOL injector until the IOL is ejected from the IOL injector. The first position may correspond to a position of the plunger tip when initially inserted into a bore of the IOL injector. The second position may correspond to a position of the plunger tip when a distal end of a plunger thread initially engages a proximal end of a bore thread formed in the IOL injector, e.g., when the plunger thread begins to engage the bore thread. The first position may correspond to a location of the plunger tip adjacent to a storage location of an IOL, and the second location may correspond to a location of the plunger tip to cause an IOL to be in a dwell location.

In some implementations, the method may also include removing a removable pin after axially pushing the plunger tip 220 from the first position to the second position and prior to axially pushing the plunger or rotating the plunger body of the plunger to further advance the plunger tip from the second position to the distal end of the IOL injector.

In some implementations, the IOL injector 10 may have one or more tabs 110, as shown, for example, in FIG. 10. A user may place one or more fingers on the tabs 110 in order to hold the IOL injector during use. In some implementations, as shown in FIG. 10, the tabs 110 may be located closer to the distal end 60 of the injector body 20 than the proximal end 50 of the IOL injector body 20.

Referring to FIGS. 14A-14D shows an example IOL injector 10 that includes an injector 20 having a collapsible portion 800 configured to reduce a length of the IOL injector 10 while advancing an IOL from a storage location 808 to a dwell location 809. The collapsible portion 800 forms a telescoping arrangement having sleeves that are telescopingly arranged with respect to one another.

Figure 14B:
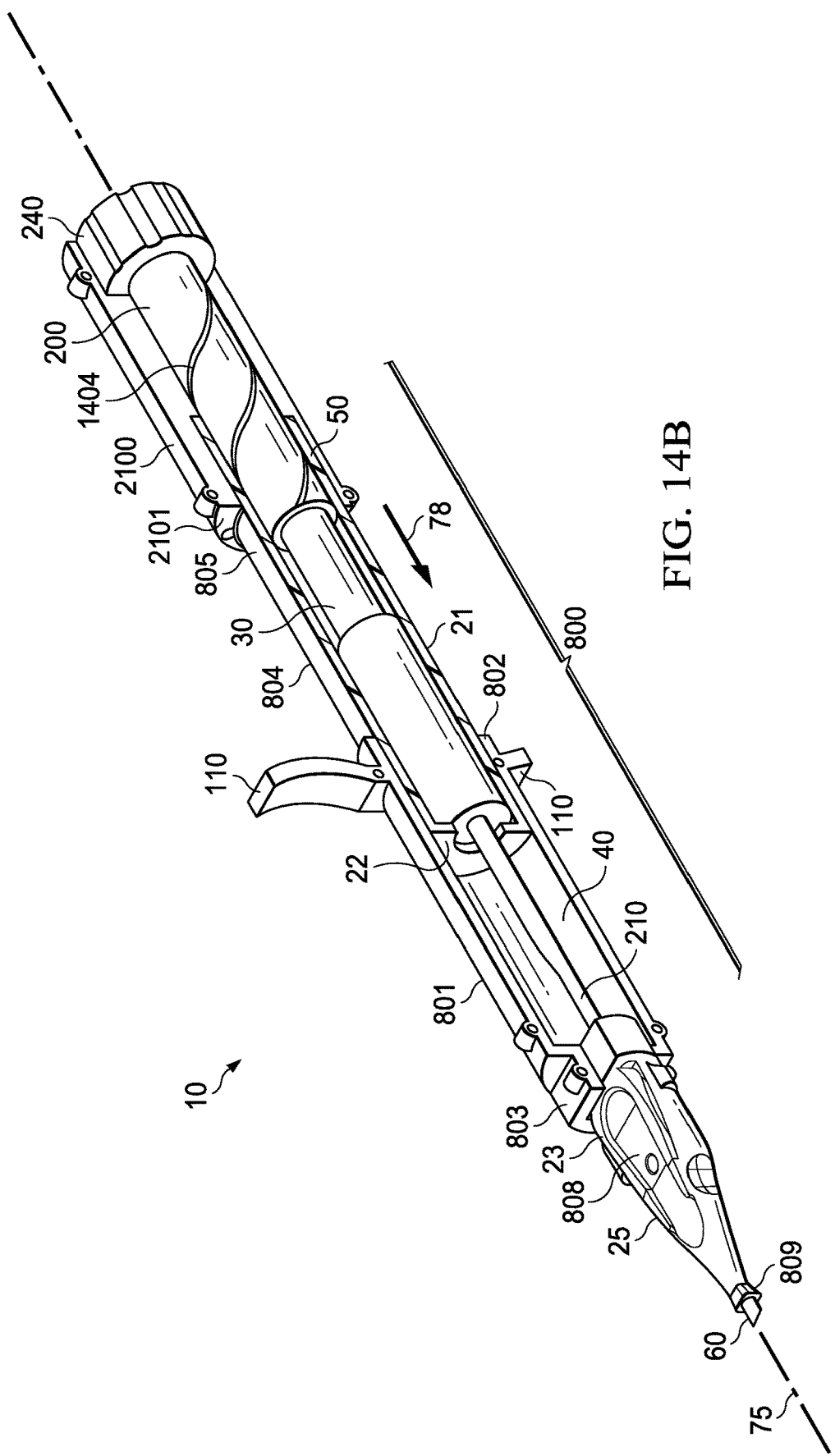
FIG. 14B shows a partial cross-sectional view of the exemplary IOL injector of FIG. 14A.
Figure 14C:
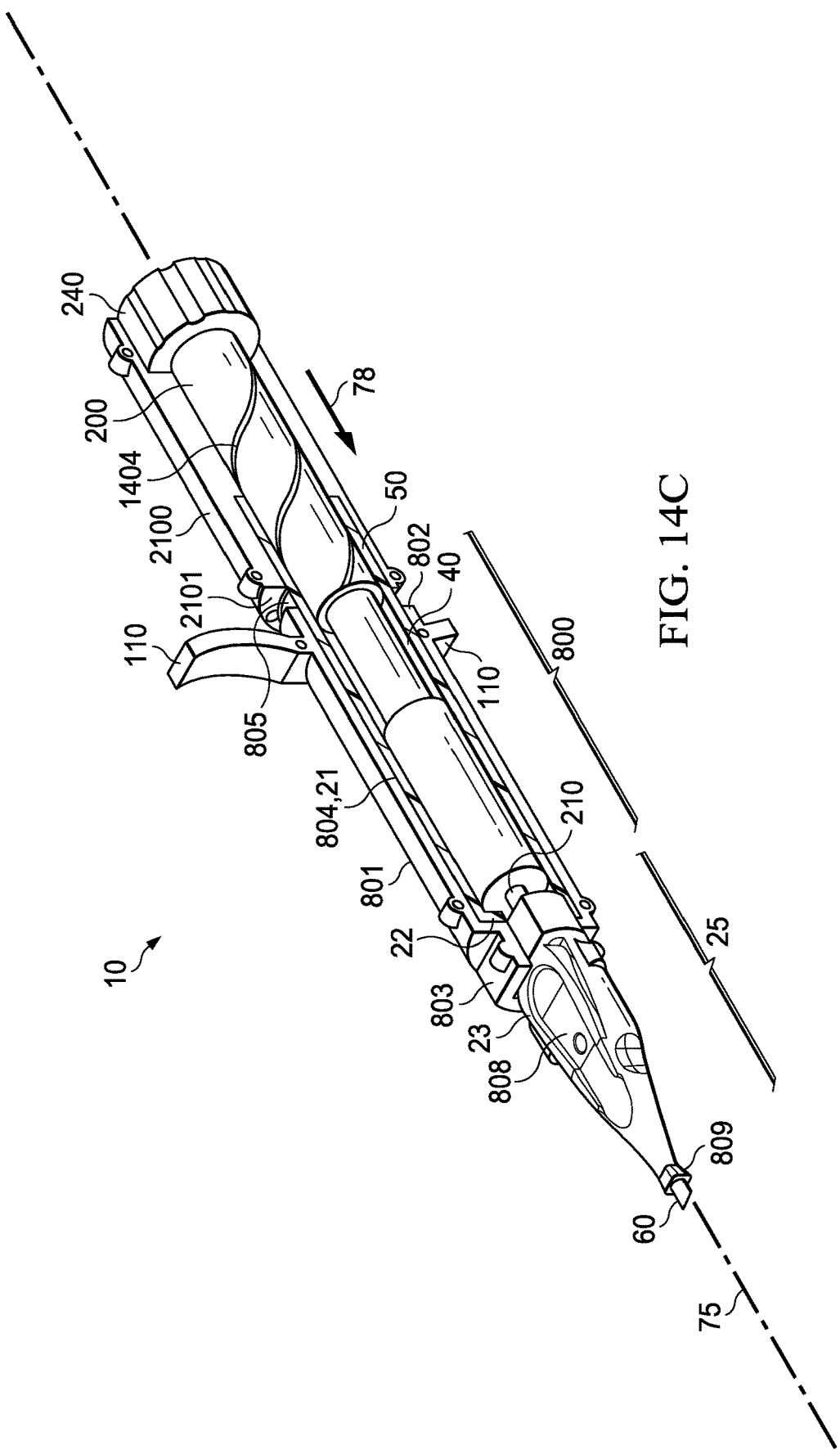
FIG. 14C is a partial cross-sectional view of the exemplary IOL injector of FIG. 14A in which the collapsible portion has been actuated.
Figure 14D:
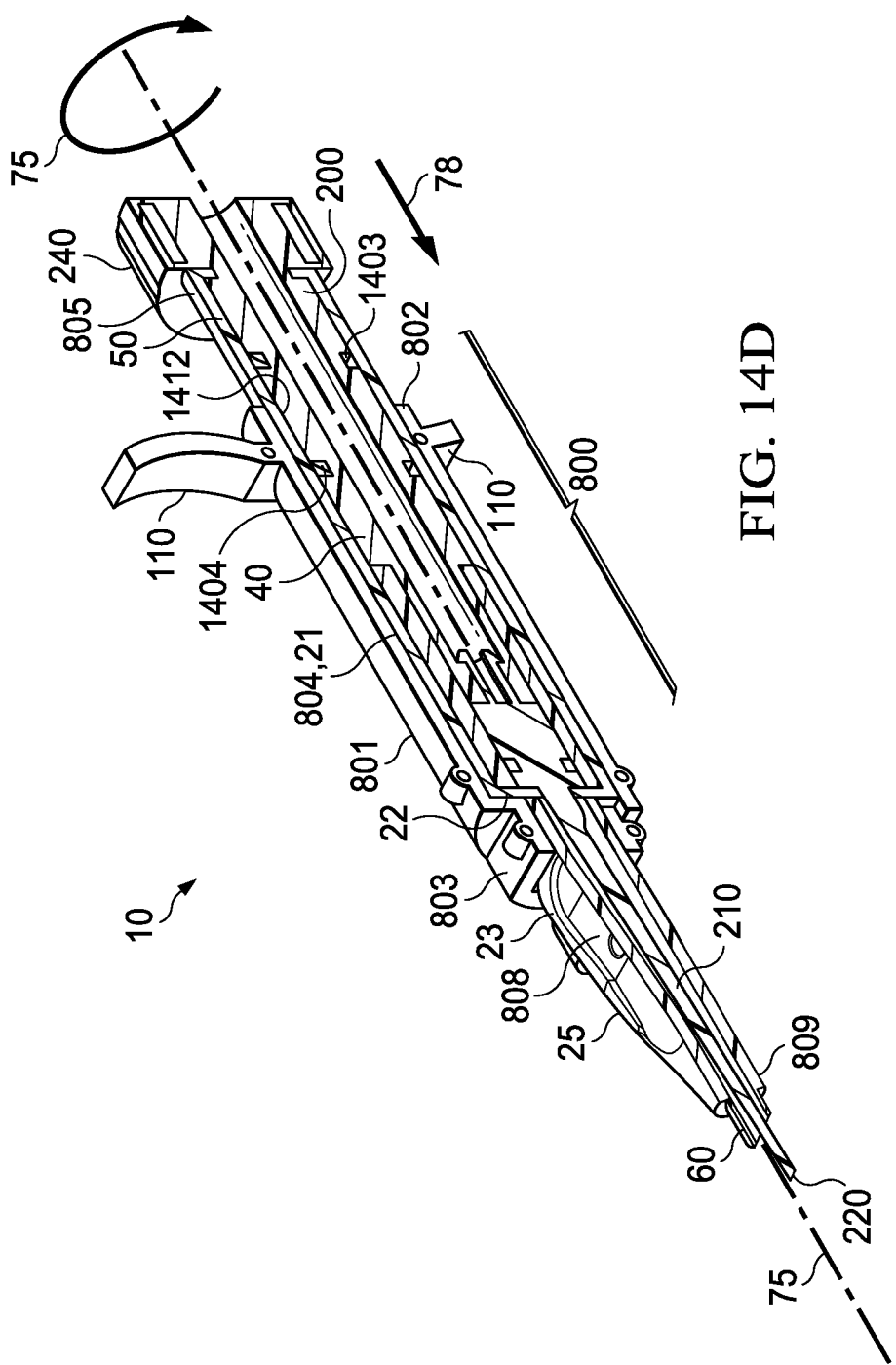
FIG. 14D is a partial cross-sectional view of the exemplary IOL injector of FIG. 14A in which the collapsible portion is actuated and the push and screw drive actuated.

The term "telescoping" generally refers to movement of a first part sliding out from, or into, a second part, where the two parts are coupled, and have an extended or uncollapsed configuration, and a shortened or collapsed configuration. A collapsible portion may include a first part and a second part that may be in the form of sleeves having different cross-sectional sizes and that are telescopingly arranged. The sleeves may be cylindrically shaped. In some instances, the sleeves may be in the form of cylinders or tubes having circular cross-sectional shapes, and the sleeves may have different diameters such that one sleeve is slideably receivable into the other sleeve. In other implementation, the sleeves may be cylinders or tubes having non-circular cross-sectional shapes but are sizes such that one sleeve is slideably receivable into the other sleeve. The sleeves may have a concentric, or nested, arrangement in which a sleeve with a smaller cross-sectional size (i.e., "inner sleeve") is received into and coaxially arranged with a sleeve having a larger cross-sectional size (i.e., "outer sleeve"). Two or more concentrically coupled telescoping sleeves may be used in a collapsible portion. The movement of one sleeve sliding out from, or into another allows respective lengthening or shortening of the collapsible portion. The lengthened, or extended configuration may be referred to as "uncollapsed," and the shortened configuration, for example, where the length of the inner sleeve is entirely or mostly contained within the outer sleeve, may be referred to as "collapsed." FIGS. 14A and 14B shows the IOL injector 10 having the collapsible portion 800 is in an uncollapsed configuration, and FIGS. 14C and 14D shows the IOL injector 10 having the collapsible portion 800 in a collapsed configuration.

For example, as shown in FIGS. 14A-14D, the collapsible portion 800 has a first sleeve 801 having a proximal end 802 and a distal end 803 and a second sleeve 804. The second sleeve 804 is received into a proximal end 802 of the first sleeve 801. The second sleeve 804 includes a proximal end 805 and a distal end 22. In this example, a distal portion of the main body 21 forms the second sleeve 804. In other implementations, the second sleeve 804 may be separate from the main body 21. The proximal end 802 of the first sleeve 801 is slideably coupled with the distal end 22 of the second sleeve 804. In some implementations, the first sleeve 801 forms an outer sleeve; the second sleeve 804 forms an inner sleeve; and the second sleeve 804 is concentrically arranged and slideable within the first sleeve 801, such that the distal portion 810 of the main body 21 slides concentrically within the first sleeve 801. In other implementations, the first sleeve 801 forms an inner sleeve; the second sleeve 804 forms an outer sleeve; and the first sleeve 801 is concentrically arranged and slideable within the second sleeve 804, such that the first sleeve 801 slides concentrically within the distal portion of the main body 21. Other configurations of the collapsible portion are possible. For example, in other implementations, the collapsible portion may include more than two sleeves that are telescoping arranged.

Referring again to FIG. 14B, the first sleeve 801 is concentrically arranged and slideable within the second sleeve 804. The first sleeve 801 and the second sleeve 804 may be coupled such that the second sleeve 804 is retained within the first sleeve 801 when the second sleeve 804 is fully extended from or is in the uncollapsed configuration with the first sleeve 801. For example, the first sleeve 801 and the second sleeve 804 may be slideably coupled by a slip joint. In an uncollapsed configuration, the distal end 22 of the second sleeve 804 is adjacent to the proximal end 802 of the first sleeve 801. In a collapsed configuration, the distal end 22 of the second sleeve 804 is adjacent to the distal end 803 of the first sleeve 801.

The IOL injector 10 includes a removable plunger cap 2100. A distal end 2101 of the plunger cap 2100 is adapted to contact the proximal end 802 of the first sleeve 801 when the collapsible portion 800 is in a collapsed configuration. When attached, the plunger cap 2100 also prevents access by a user to the plunger 30, thereby preventing inadvertent axial advancement of the plunger 30 by the user, either by depression or by rotation of the plunger body 200 of the plunger 30. Placing the collapsible portion 800 in the collapsed configuration from the uncollapsed configuration, as shown in FIG. 14C, advances the plunger 30 form a first position in which a plunger tip 220 of a plunger rod 210 is proximally adjacent to an IOL storage location 808 to a location proximally adjacent to an IOL dwell location 809. Actuation of the collapsible portion 800 into the collapsed configuration is operable to cause the plunger tip 220 to advance an IOL located in the storage location 808 to the dwell location 809. The plunger cap 2100 is removable and is intended to be removed following placing the collapsible portion 800 of the IOL injector 10 into the collapsed configuration. With the plunger cap 2100 removed, the plunger 30 may then be advanced to complete advancement of the IOL out of the IOL injector, such as into an eye of a patient. Accordingly, in some implementations, removal of the plunger cap 2100 is needed before the plunger tip 220 can be axially advanced from the second position towards the distal end 60 of the nozzle 25 by axially pushing or rotating the plunger body 200 of the plunger 30.

The proximal end 23 of the nozzle 25 is coupled to the distal end 803 of the first sleeve 801. In some implementations, the plunger tip 220 may be 5 mm to 20 mm proximal to an IOL in the storage location 808 when the collapsible portion 800 is in the uncollapsed configuration, and the plunger tip 200 may be proximally adjacent and in contact with a trailing, or proximally oriented, haptic of the IOL (or a proximal edge of an optic of a two-piece IOL) in the dwell location 809 when the collapsible portion 800 is in the collapsed configuration.

As described herein, for example, the dwell location 809 position may be indicated by positioning of the IOL 70, or part thereof, relative to a demarcation formed on the nozzle 25, such as the demarcation 1900 described above. Further, placement of the IOL into the dwell location 809 may correspond to engagement of the distal end 2101 of the plunger cap 2100 with the proximal end 802 of the first sleeve 801 (which corresponds to the collapsed configuration of the collapsible portion 800), prior to an application of an axial or rotational force to the plunger body 200 of the plunger 30. In other implementations, relative movement of the first sleeve 801 and the second sleeve 804 that corresponds to less than the collapsed configuration may result in positioning the IOL into the dwell location 809.

In some implementations, a length of the IOL injector 10 in the collapsed configuration may be 10 to 20% shorter than the length of the IOL injector in the uncollapsed configuration. However, the scope of the disclosure is not so limited. Rather, the percentage values are provided merely as example. In other implementations, the relative lengths of an IOL injector within the scope of the present disclosure may be less than 10% or greater than 20%, FIG. 14C shows the IOL injector 10 in which the second sleeve 804 is slid into the first sleeve 801, resulting in the collapsible portion 800 being in the collapsed configuration. With the collapsible portion 800 in the collapsed configuration, the distal end 22 of the second sleeve 804 is adjacent to the distal end 803 of the first sleeve 801; the distal end 2101 of the plunger cap 2100 is in contact with the proximal end 802 of the first sleeve 801; and the plunger tip 220 is in the second position proximally adjacent to the dwell location 809

FIG. 14D shows the IOL injector 10 with the plunger cap 2100 removed and following rotation of the main body 200 of the plunger 30 in the direction of the arrow 75. As a result of the axial advancement of the plunger 30 due to of rotation in the direction of arrow 75, the plunger tip 220 is advanced from the dwell location 809 towards the distal end 60 of the nozzle 25. As rotation of the main body 200 of the plunger 30 continues, an IOL contained in the IOL injector 10 continues to advance and, ultimately, is ejected from the IOL injector, e.g., injected into an eye of a patient. Accordingly, removal of the plunger cap 2100 unlocks of the plunger body 200 of the plunger 30, allowing advancement of the IOL from the dwell location 809 and ejection of the IOL form the IOL injector 10.

As shown in FIG. 14D, the plunger body 200 includes a plunger thread 1404. The plunger thread 1404 may engage a pin formed on an interior wall of the main body 21 or a threaded surface formed on the inner wall of the main body 21.

Figure 16:
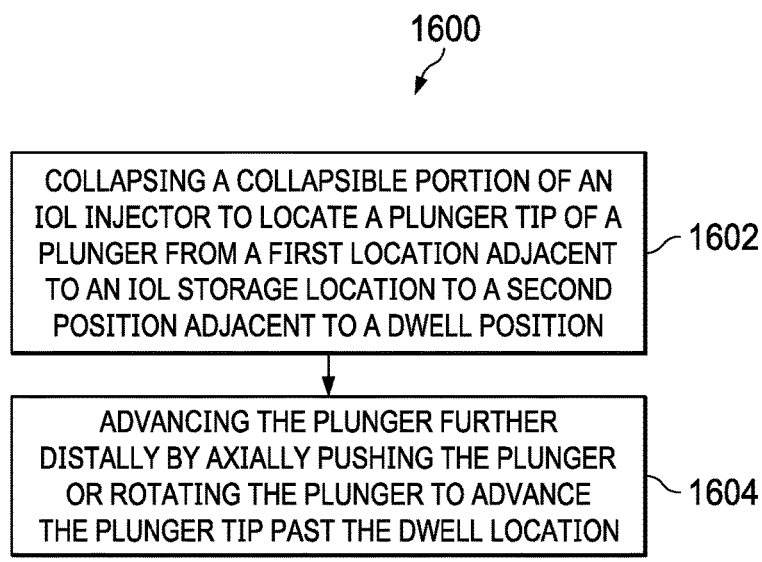
FIG. 16 is another example method of using an IOL injector.

Accordingly, the present disclosure also relates to methods of advancing an IOL from a storage location to a dwell location, and ejecting the IOL from the IOL injector, e.g., into an eye of a patient. An example method 1600 shown in FIG. 16 include, at step 1602, collapsing a collapsible portion of the IOL injector by axially sliding a first sleeve relative to a second sleeve. Collapsing the collapsible portion locates a plunger tip of a plunger from a first position adjacent to a storage location to a second position adjacent to a dwell location. As shown in the example of FIGS. 14A to 14D, the collapsing the collapsible portion 800 is performed in the direction of arrow 78. It will be understood that the method step of collapsing the collapsible portion does not involve sliding a plunger in relation to an injector body. In addition, collapsing the collapsible portion in this way results in a shorter IOL injector for use in ejecting an IOL 70 from the IOL injector, such as into an eye of a patient. Thus, collapsing the collapsible portion improves ergonomics by reducing the overall length of the IOL injector 10. By collapsing the collapsible portion, a plunger tip of the plunger is advanced from a first location adjacent to a storage location in the IOL injector to a dwell location in the IOL injector.

At step 1604, the plunger may be advanced further distally by axially pushing the plunger or rotating the plunger. Further advancement of the plunger is operable to advance an IOL in the dwell location past the dwell location and ultimately out of the IOL injector, such as into an eye of a patient.

The various implementations of the IOL injectors described herein and within the scope of the present disclosure may be configured to deliver an IOL base and/or an IOL optic of a multi-piece IOL or configured to deliver a single-piece IOL. Various implementations of the IOL injectors and associated methods described herein may be used with an IOL base and/or the optic that are manually loaded into the IOL injector by a user or pre-loaded there prior to delivery by a user.

Advantages of the IOL injectors described herein include but are not limited to the following. The IOL injectors described herein include a combination push and screw drive that is operable to advance plunger both by pushing and by rotating the plunger. This combination brings with it the benefits of a threaded engagement, which adds smoothness and controlled motion throughout the delivery of an IOL out of the IOL injector due to the mechanical transfer of force through the threads. IOL injectors having a threaded engagement typically require the use of two hands during the procedure, which can result in the user having more control during the procedure. The IOL injectors described herein are also compatible with both single handed and two-handed operation due to the ability to advance the plunger by applying an axial force to the plunger.

The combination push and screw drives described herein provide a solution to generate axial forward motion for an IOL in a smooth and controlled manner. The threads provide a built-in damping as the threads limit a speed with which the IOL can be advanced.

The IOL injector described herein offers flexibility to the user such that the user is able to choose whether to advance the IOL to the dwell location using an axial push and then advance the IOL to ejection from the IOL injector using either an axial push or a rotation applied to the plunger. This IOL injectors as described herein provide flexibility and are compatible with users who utilize different techniques and skills while operating an IOL injector.

The above-disclosed subject matter is to be considered illustrative, and not restrictive, and the appended claims are intended to cover all such modifications, enhancements, and other implementations that fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector comprising:
an injector body comprising:
  a main body comprising:
    a bore; and
    an interior wall defined by the bore, the interior wall including a distal portion and a proximal portion;
  a nozzle coupled to a distal end of the main body, the nozzle comprising:
    a passage in fluid communication with the bore; and
    a distal opening in fluid communication with the passage;
a plunger received in the bore and comprising:
  a plunger body;
  a plunger rod coupled to a distal end of the plunger body; and
  a plunger tip formed at a distal end of the plunger rod and adapted to contact an IOL, one of the interior wall and the plunger body including a threaded surface and the other of the interior wall and the plunger body including a feature adapted to engage the threaded surface to produce axial movement of the plunger in response to axial movement or rotation of the plunger body; and a plunger cap removably couplable to the plunger and adapted to prevent engagement of the threaded surface and the feature adapted to engage the threaded surface.

2. The IOL injector of claim 1, wherein the interior wall comprises a distal wall portion and a proximal wall portion and wherein the threaded surface or the feature adapted to engage the threaded surface is disposed in the distal wall portion of the interior wall.

3. The IOL injector of claim 1, wherein the feature adapted to engage the threaded surface is a second threaded surface.

4. The IOL injector of claim 1, wherein the threaded surface includes a pitch that varies along the main body.

5. The IOL injector of claim 4, wherein the pitch is wider at a proximal end of the main body and is narrower at a distal end of the main body.

6. The IOL injector of claim 1, wherein the plunger further comprises a flange rotationally decoupled from the plunger body.

7. The IOL injector of claim 1, wherein the interior wall comprises a distal wall portion and a proximal wall portion, wherein the plunger is slideable through the bore along the proximal wall portion of the interior wall from a first location where the plunger tip is proximally adjacent to a storage location in the nozzle to a second position where the plunger tip is proximally adjacent to a dwell location, the second position corresponding to initial engagement of the threaded surface and the feature adapted to engage the threaded surface.

8. The IOL injector of claim 1, wherein the injector body further comprises one or more tabs adapted to be engaged by one or more fingers.

9. The IOL injector of claim 8, wherein the one or more tabs are located closer to a distal end of the injector body than to a proximal end of the injector body.

* * * * *